US012266849B2

(12) United States Patent
Rauhala

(10) Patent No.: US 12,266,849 B2
(45) Date of Patent: Apr. 1, 2025

(54) GOGGLE STRAP TO IMPROVE RADIO FREQUENCY RECEPTION AND AUDIO SPEAKER INTEGRATION

(71) Applicant: Finnovate Group LLC, Solana Beach, CA (US)

(72) Inventor: Kari Kristian Rauhala, Solana Beach, CA (US)

(73) Assignee: Finnovate Group LLC, Solana Beach, CA (US)

( * ) Notice: Subject to any disclaimer, the term of this patent is extended or adjusted under 35 U.S.C. 154(b) by 0 days.

(21) Appl. No.: 18/109,181

(22) Filed: Feb. 13, 2023

(65) Prior Publication Data
US 2024/0266717 A1    Aug. 8, 2024

Related U.S. Application Data

(60) Provisional application No. 63/309,465, filed on Feb. 11, 2022.

(51) Int. Cl.
H01Q 1/27     (2006.01)
H01Q 1/38     (2006.01)
H01Q 9/28     (2006.01)

(52) U.S. Cl.
CPC ............ H01Q 1/273 (2013.01); H01Q 1/38 (2013.01); H01Q 9/285 (2013.01)

(58) Field of Classification Search
CPC ............ H01Q 1/273; H01Q 1/38; H01Q 1/24; H01Q 9/285; G02C 3/003; G02C 5/001; G02C 11/10
See application file for complete search history.

(56) References Cited

U.S. PATENT DOCUMENTS 7,310,427 B2 *  12/2007  Retchin ............... H04R 1/1066
                                                381/151
2019/0089469 A1 *  3/2019  Goren ................... H04B 13/02

* cited by examiner

Primary Examiner — Robert Karacsony
(74) Attorney, Agent, or Firm — FisherBroyles LLP; James P. Cleary

(57) ABSTRACT

An audio player device for a pair of goggles having two eye shields. The audio player device includes an elastomeric strap configured for being coupled with each of the eye shields of the pair of googles and for being expanded around a wearer's head to secure and position the pair of goggles to the wearer. The device further includes an antenna integrated with at least a portion of the elastomeric strap. The antenna is configured to stretch upon expansion of the elastomeric strap, and to receive radio frequency (RF) signals. The device further includes an audio player device attached with the elastomeric strap and connected to the antenna to receive and play the RF signals.

10 Claims, 3 Drawing Sheets

GOGGLE STRAP TO IMPROVE RADIO FREQUENCY RECEPTION AND AUDIO SPEAKER INTEGRATION

CROSS-REFERENCES TO RELATED APPLICATIONS

The present application claims priority of U.S. Provisional Application No. 63/309,465, filed Feb. 11, 2022, and entitled "GOGGLE STRAP TO IMPROVE RADIO FREQUENCY RECEPTION AND AUDIO SPEAKER INTEGRATION", the entirety of which is incorporated by reference herein.

BACKGROUND

Various activities, such as swimming, water polo, synchronized swimming, surfing, and the like occur in an aquatic environment. In today's times, most people want or need to be connected to a radio frequency (RF) communication device, such as a mobile phone, smart watch, media player device, etc. However, in an aquatic environment, RF reception is typically very poor due to signal absorption and attenuation, as well as a difficulty for radio frequency signal propagation through water.

There are some products on the market that allow persons in an aquatic environment to listen to audio, such as music files, podcasts, or the like. These products usually include water-proof headphones such as earbuds or the like, which are in turn connected to an audio source. The audio source is typically a digital media player that is worn by a person and connected directly with the water-proof headsets or earphones, where the digital media player stores audio files locally, most likely from a previous download to the digital media player, and plays the locally stored files to the person's headset or earphones.

SUMMARY

This document discloses a goggle, i.e., eyewear that can be worn to protect a wearer's eyes in a potentially difficult environment for the wearer, such as water or any aquatic environment, and a strap for the goggle to keep the goggle secured to the wearer's head, with a built-in, integrated RF antenna to improve RF reception in the environment. The goggle and/or goggle strap can further include a built-in digital media player and/or speakers, such as headphones. The headphones can be "earbud" type headphones that have a sound driver that is insertable into the wearer's ear, or conduction type headphones that conduct sound through a wearer's head and head bones proximate the wearer's ear.

In some aspects, an audio player device for a pair of goggles having two eye shields is disclosed. The audio player device includes an elastomeric strap configured for being coupled with each of the eye shields of the pair of googles and for being expanded around a wearer's head to secure and position the pair of goggles to the wearer. The device further includes an antenna integrated with at least a portion of the elastomeric strap. The antenna is configured to stretch upon expansion of the elastomeric strap, and to receive radio frequency (RF) signals. The device further includes an audio player device attached with the elastomeric strap and connected to the antenna to receive and play the RF signals.

In other aspects, a goggle strap for a pair of goggles having two eye shields is disclosed. The goggle strap includes an elastomeric strap configured for being coupled with each of the eye shields of the pair of googles and for being expanded around a wearer's head to secure the pair of goggles to the wearer. The goggle strap further includes an antenna integrated with at least a portion of the elastomeric strap, the antenna being configured to stretch upon expansion of the elastomeric strap, and to receive radio frequency (RF) signals.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

This document describes a goggle, and more particularly a goggle strap, with a built-in, integrated radio frequency (RF) antenna to improve RF reception in an aquatic or other difficult environment in which to receive RF signals. The goggle and/or goggle strap can further include a built-in digital media player and/or speakers, such as headphones, earbuds or the like.

Figure 1:
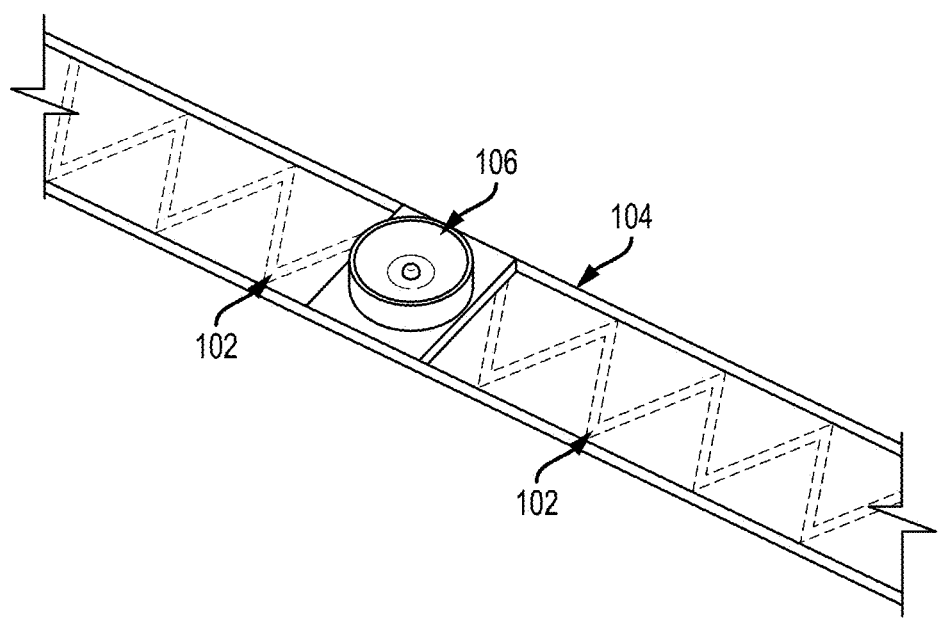
FIG. 1 illustrates an example of a zigzag-type antenna that can be molded with rubber or silicone and made into a goggle strap with an external RF connector.

FIG. 1 illustrates a portion of a goggle 100 having an antenna 102 in a zigzag configuration and that can be molded on or in rubber or silicone and provided on or in at least a portion of a goggle strap 104. The goggle strap 104 can also include an external RF connector 106 connected with the antenna 102. In some implementations, the antenna 102 can be over-molded onto the goggle strap 104. In other implementations, the antenna 102 can be embedded or co-molded with the goggle strap 104.

In preferred implementations, one or more antennas 102 are molded onto, or into, one or more elastomeric goggle straps 104 for use with a swim goggle 100 in an aquatic environment. Each antenna 102 can be a wire or a dipole-type antenna. The coupling of the one or more antennas 102 can be by co-molding or embedding inside the goggle strap 104. The antenna 102 can be connected or coupled with a receiver (passively resonance-coupled or via a connector 106). The antenna 102, whether embedded in or overlaid on the goggle strap 104 acts as an additional or external antenna for an RF receiver to improve RF reception in the aquatic environment.

In preferred implementations, the RF receiver, via antenna 102 on or in the goggle strap 104, receives a signal, such as audio signals, from a transmitter, such as a mobile phone or other media player, over a wireless connection, such as a Bluetooth connection or other short-range wireless connection. The antenna 102 provides received RF signals to an audio player device via connector 106.

Figure 2:
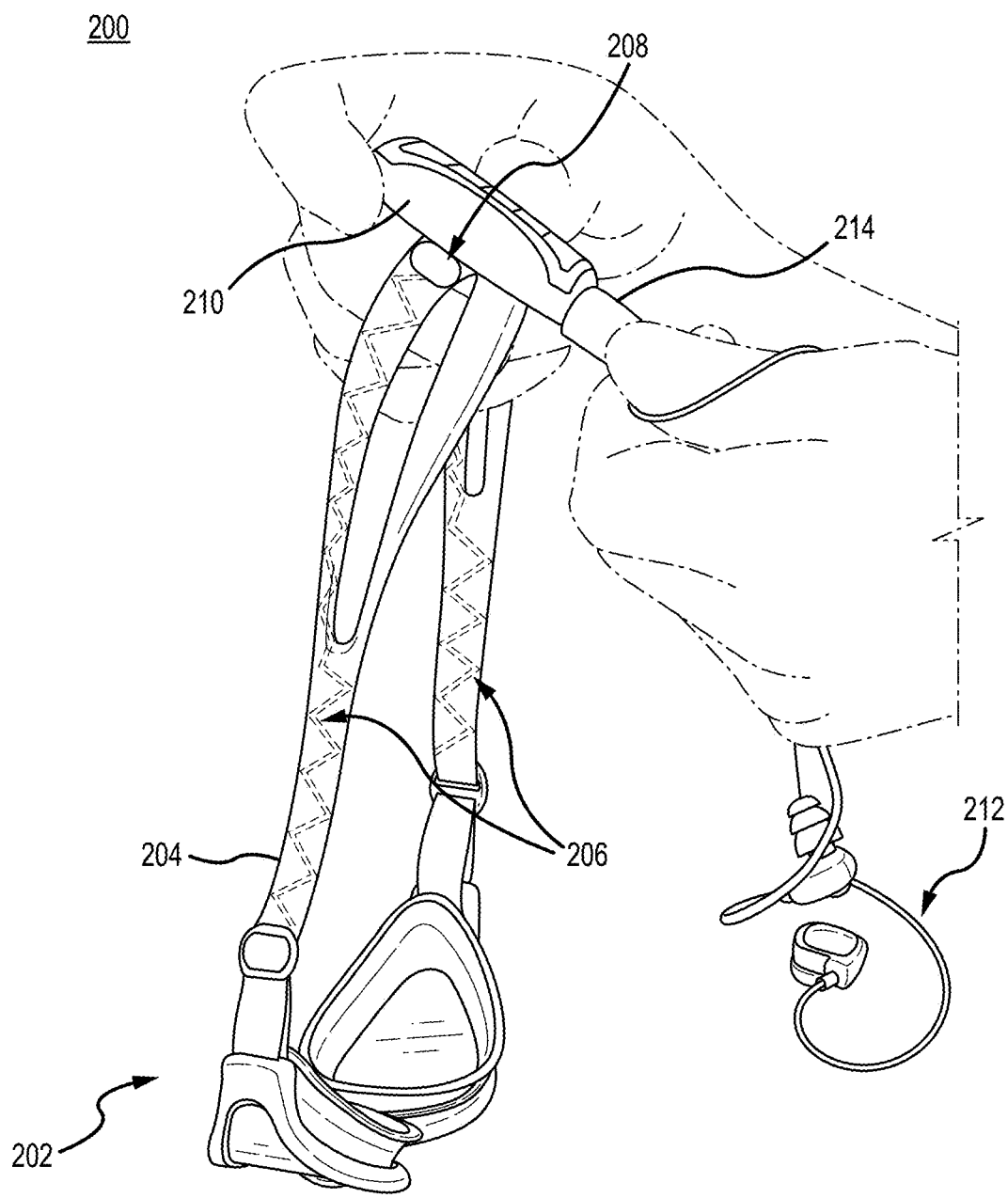
FIG. 2 shows an audio system that is integrated with a pair of goggles having a pair of eye shields.

FIG. 2 shows an audio system 200 that is integrated with a pair of goggles 202 having a pair of eye shields. The goggles 202 have a goggle strap 204. The goggle strap 204 is preferably elastomeric, particularly longitudinally, so as to be able to stretch and fit around a wearer's head. The goggle strap 204 can be made of an elastomer material such as rubber or silicone or the like. The goggle strap 204 can have one or more strap members.

The goggle strap 204 further includes an antenna 206 that is embedded in, or overmolded onto at least one strap member of the goggle strap 204. The antenna 206 can be a wire or a dipole antenna. In some implementations, the antenna 206 is provided in a zigzag configuration, which allows the antenna to expand and return along with the goggle strap 204 when it is placed around the wearer's head to properly position the goggles 202 over the wearer's eyes. Further, the zigzag configuration allows the antenna 206 to have a predetermined overall length, which can be tuned to a particular transmission frequency of RF signals to be received. The zigzag configuration can be angular, such as a sawtooth shape, or rounded.

The audio system 200 further includes an audio player 210, such as a digital media player device, that is coupled with the antenna 206 via connector 208. The audio player 210 can include a memory for storing digital audio or other media files, such as video, which can be played to the wearer through headphones 212 or even by a screen or interface within the goggles 202. Alternatively, the audio player 210 can receive wireless RF signals via antenna 206 and connector 208 for real-time processing and playing to the wearer. The headphones 212 can be earbud type headphones, and can be waterproof so as to accommodate an aquatic environment. The headphones 212 can be wireless, or be connected with the audio player 210 via plug 214. The plug 214 can also form a watertight seal so as to be waterproof.

Figure 3:
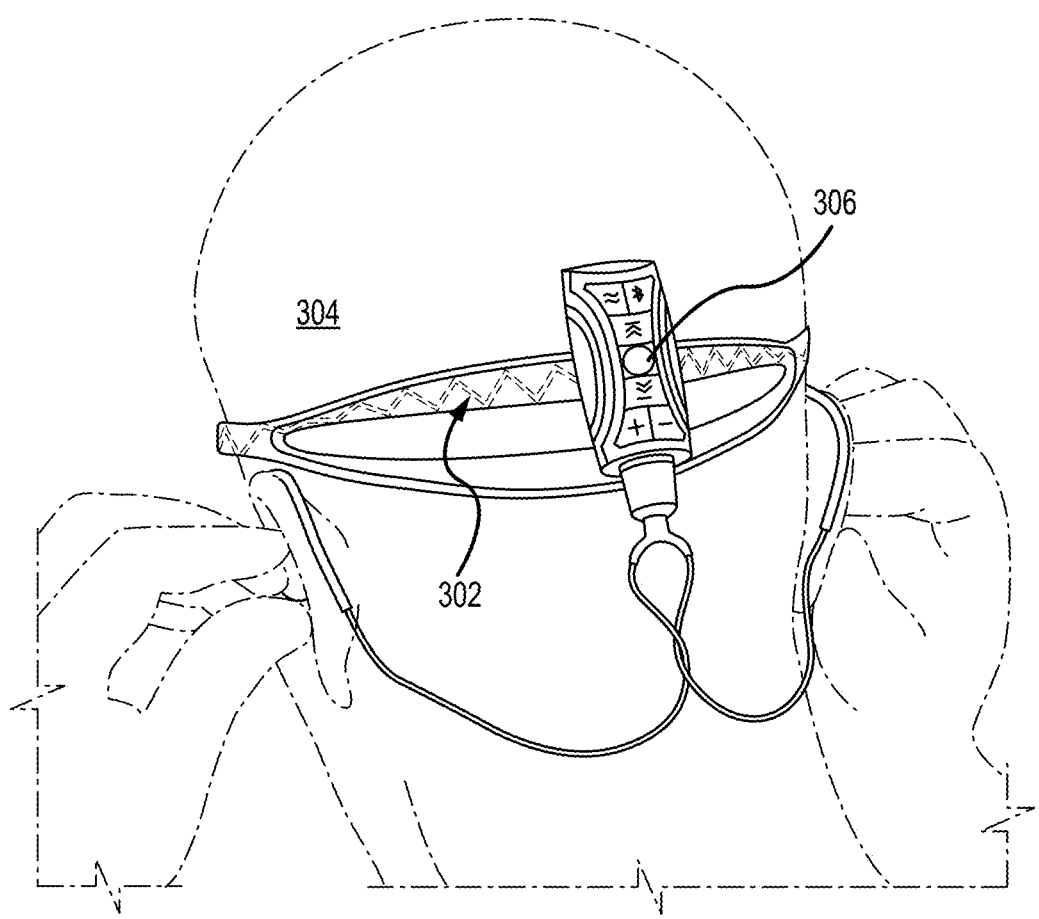
FIG. 3 illustrates an antenna inside or on a goggle strap that is positioned to reach around on both sides of a wearer's head.

As shown FIG. 3, an antenna 302 inside a goggle strap 304 is positioned to reach around on both sides of a wearer's head, and therefore some parts of the antenna 302 can be positioned above the surface of the aquatic environment while the wearer is in the aquatic environment performing an activity such as swimming. Accordingly, RF reception is increased by having better reception, by ensuring that at least a portion or part of the antenna 302 is positioned at or above a surface of the water.

The wire inside the goggle strap 304 is routed or positioned in such a way that enables the elastomeric strap to stretch without breaking the antenna. Accordingly, in some implementations, the antenna wire is formed in a zigzag (i.e., up-and-down) orientation along a length of the goggle strap 304. This zigzag wire length can be designed or tuned to match certain frequencies or signal wavelengths, such as ¼ wavelength zigzag.

An RF receiver/audio player 306 is coupled with the antenna 302. The RF receiver 306 can have a special connector to couple with an external antenna to improve RF reception. The connector can be waterproof. The RF receiver 306 can be attached to the strap 304 and connector with a clip or other attachment mechanism.

The antenna wire inside the strap can also be used to conduct audio signals to speakers, such as headphones or the like. Headphones and an audio player can also be integrated into the goggles for a diverse range of environments (swim, dive, snow, etc.). The audio player and RF receiver 306 can be embedded in the goggle strap 304 as well.

Although a few embodiments have been described in detail above, other modifications are possible. Other embodiments may be within the scope of the following claims.

The invention claimed is:

1. A goggle strap for a pair of goggles having two eye shields, the goggle strap comprising:
    an elastomeric strap configured for being coupled with each of the eye shields of the pair of goggles and for being expanded around a wearer's head to secure the pair of goggles to the wearer; and
    an antenna integrated along a length of at least a portion of the elastomeric strap, the antenna being configured in a zigzag configuration along a length of the portion of the elastomeric strap so as to stretch upon lengthwise expansion of the elastomeric strap, and to receive radio frequency (RF) signals.

2. The goggle strap in accordance with claim 1, wherein the antenna is a wire.

3. The goggle strap in accordance with claim 1, wherein the antenna is a dipole antenna.

4. An audio player system comprising:
    a pair of goggles having two eye shields;
    an elastomeric strap configured for being coupled with each of the eye shields of the pair of goggles and for being expanded around a wearer's head to secure and position the pair of goggles to the wearer;
    an antenna integrated along a length of at least a portion of the elastomeric strap, the antenna being configured in a zigzag configuration along a length of the portion of the elastomeric strap so as to stretch upon lengthwise expansion of the elastomeric strap, and to receive radio frequency (RF) signals; and
    an audio player device attached with the elastomeric strap and connected to the antenna to receive and play the RF signals.

5. The audio player system in accordance with claim 4, further comprising headphones connected with the audio player device.

6. The audio player system in accordance with claim 4, wherein the antenna is a wire.

7. The audio player system in accordance with claim 4, wherein the antenna is a dipole antenna.

8. The audio player system in accordance with claim 5, wherein the connection between the headphones and the audio player device is waterproof.

9. The audio player system in accordance with claim 4, wherein the connection between the audio player device and the antenna is waterproof.

10. An audio player device for a pair of goggles having two eye shields, the audio player device comprising:
    an elastomeric strap configured for being coupled with each of the eye shields of the pair of goggles and for being expanded around a wearer's head to secure and position the pair of goggles to the wearer;
    an antenna integrated along a length of at least a portion of the elastomeric strap, the antenna being configured in a zigzag configuration along a length of the portion of the elastomeric strap so as to stretch upon lengthwise expansion of the elastomeric strap, and to receive radio frequency (RF) signals; and
    an audio player device attached with the elastomeric strap and connected to the antenna to receive and play the RF signals.

* * * * *